United States Patent
Park et al.

(10) Patent No.: US 10,383,904 B2
(45) Date of Patent: Aug. 20, 2019

(54) COMPOSITION FOR IMPROVING HEALTH AND QUALITY OF LIFE OF WOMEN CONTAINING GINSENG BERRY EXTRACT

(71) Applicant: Amorepacific Corporation, Seoul (KR)

(72) Inventors: Chan Woong Park, Yongin-si (KR); Su Hwan Kim, Yongin-si (KR); Jeong Hwa Jang, Yongin-si (KR); Hyun Jung Shin, Yongin-si (KR); Sun Mi Kim, Yongin-si (KR); Wan Gi Kim, Yongin-si (KR); Sang Jun Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 817 days.

(21) Appl. No.: 14/779,599

(22) PCT Filed: Apr. 2, 2014

(86) PCT No.: PCT/KR2014/002853
§ 371 (c)(1),
(2) Date: Sep. 24, 2015

(87) PCT Pub. No.: WO2014/163402
PCT Pub. Date: Oct. 9, 2014

(65) Prior Publication Data
US 2016/0058811 A1    Mar. 3, 2016

(30) Foreign Application Priority Data

Apr. 2, 2013 (KR) .................... 10-2013-0035810
Apr. 2, 2014 (KR) .................... 10-2014-0039272

(51) Int. Cl.
*A61K 36/258* (2006.01)
*A23L 33/105* (2016.01)

(52) U.S. Cl.
CPC .......... *A61K 36/258* (2013.01); *A23L 33/105* (2016.08); *A23V 2002/00* (2013.01)

(58) Field of Classification Search
CPC . A23L 33/105; A23V 2002/00; A23V 36/258; A61K 36/258
See application file for complete search history.

(56) References Cited

U.S. PATENT DOCUMENTS

2012/0076874 A1* 3/2012 Jeon .................. A61K 36/79
424/725

FOREIGN PATENT DOCUMENTS

| KR | 10-2005-0076057 A | 7/2005 |
| KR | 10-2007-0051934 A | 5/2007 |
| KR | 10-2008-0094540 A | 10/2008 |
| KR | 10-2011-0079564 A | 7/2011 |

OTHER PUBLICATIONS

Sung and Yang, Korean J Food Sci. Technol. vol. 17. No. 3 (1985), pp. 227-231 (w. English abstract) (Year: 1985).*
C. I. Coleman et al., "The effects of Panax ginseng on quality of life", Journal of Clinical Pharmacy and Therapeutics, 2003, pp. 5-15, vol. 28.
International Searching Authority, International Search Report of PCT/KR2014/002853 dated Jul. 31, 2014 [PCT/ISA/210].

* cited by examiner

*Primary Examiner* — Aaron J Kosar
(74) *Attorney, Agent, or Firm* — Sughrue Mion, PLLC (57) ABSTRACT

The present invention relates to a composition which improves the quality of life of women by containing a ginseng berry extract as an active ingredient, and more specifically, to a composition which promotes the general psychological and physical health of women and improving the sexual function and sex life satisfaction women.

6 Claims, 3 Drawing Sheets

COMPOSITION FOR IMPROVING HEALTH AND QUALITY OF LIFE OF WOMEN CONTAINING GINSENG BERRY EXTRACT

CROSS REFERENCE TO RELATED APPLICATIONS

This application is a National Stage of International Application No. PCT/KR2014/002853, filed Apr. 2, 2014, claiming priority based on Korean Patent Application Nos. 10-2013-0035810, filed Apr. 2, 2013 and 10-2014-0039272, filed Apr. 2, 2014, the contents of all of which are incorporated herein by reference in their entirety.

TECHNICAL FIELD

The present invention relates generally to a composition for improving the health and quality of life of women, which contains a ginseng berry extract as an active ingredient, and more particularly, to a composition for promoting the general psychological and physical health of women and improving the sexual function, sexual satisfaction and quality of life (QOL) of women.

BACKGROUND ART

Ginseng (Panax ginseng C. A. Meyer) is a plant belonging to the genus Panax of the family Araliaceae, and is a herbal medicine which has been used from about 2,000 years ago in Korea, China, Japan and the like in order to prevent diseases and to extend life span. The effects of ginseng, known to date, include action on the central nervous system, anti-carcinogenic action, anticancer activity, immune function regulatory action, anti-diabetic action, liver function-improving action, cardiovascular disorder-relieving and anti-atherogenic actions, blood pressure-controlling action, alleviation of menopausal disorders and osteoporosis, anti-stress and anti-fatigue actions, antioxidant activity and aging inhibitory effects (Recent Korean Ginseng, "Components and Effects", the Korea Ginseng Research Institute, 56-112, 1996).

It is known that ginsenosides, which are representative of the physiologically active components of ginseng, are uniformly distributed in the above-ground and underground parts of ginseng, and particularly the content and composition of ginsenosides vary depending on ginseng parts, including ginseng roots, ginseng leaves and ginseng berries (Attele A S et al, Biochem Pharmacol, 58; 1685-1693, 1999). Particularly, it was reported that the ginseng berries showed better antidiabetic effects than those of the ginseng roots due to the components and contents thereof different from the ginseng roots (Dey L. et al., Phytomedicine, 10; 600-605, 2003).

DISCLOSURE

Technical Problem

The present inventors have conducted studies on the various physiological activities of extracts from ginseng berries that are the above-ground parts of ginseng in addition to ginseng roots that are the underground parts of ginseng. As a result, the present inventors have found that an extract from ginseng berries has the effects of improving general physical function and alleviating menopausal symptoms and also improving the sexual function and satisfaction of women, due to its components and composition different from those of general ginseng and red ginseng, thereby completing the present invention.

Therefore, it is an object of the present invention to provide a composition which can improve the happiness and quality of life of women by increasing the health index of women and particularly improving the sexual function of women.

Technical Solution

In order to accomplish the above object, the present invention provides a composition for promoting the physical health of women, which contains a ginseng berry extract as an active ingredient.

The present invention also provides a composition for promoting the psychological health of women, which contains a ginseng berry extract as an active ingredient.

The present invention also provides a composition for improving the sexual function of women, which contains a ginseng berry extract as an active ingredient.

Advantageous Effects

A ginseng berry extract according to the present invention can improve general physical function, alleviate menopausal symptoms, and also improve the sexual function and satisfaction of women.

BEST MODE

The present invention relates generally to a composition capable of improving the quality of life of women, and more particularly, to a composition capable of improving the physical and psychological health states of women, and the sexual function of women as evaluated by the psychological general well-being index (PGWBI) and the female sexual function index (FSFI).

The composition according to the present invention can promote the general physical health status of women by improving peripheral blood circulation and alleviating chronic fatigue, and particularly, can assist in the alleviation of menopausal symptoms.

Furthermore, the composition according to the present invention can promote the psychological health state by reducing mental anxiety, depression and the like and improving self-control ability while giving vitality to life.

In addition, the composition according to the present invention can improve the sexual function of women to thereby increase the sexual satisfaction of women.

The composition according to the present invention is characterized in that it contains a ginseng berry extract in an amount of 1-100 wt % based on the total weight of the composition depending on the formulation of the composition.

The ginseng berry extract that is used in the present invention can be prepared by extracting all the parts including skin and flesh of ginseng berries. For example, the ginseng berry extract that is used in the present invention may be an extract obtained from the flesh and skin of ginseng berries, excluding ginseng seeds, or may be an extract obtained from only the flesh of ginseng berries, or may be an extract obtained from only the skin of ginseng berries.

In addition, an extraction method for preparing the ginseng berry extract is not specifically limited, as long as it is a conventional method that is used in the art. For example, the ginseng berry extract can be prepared by extraction with ethanol.

The composition according to the present invention may be formulated as a pharmaceutical composition or a food composition in the form of tablets, pills, capsules, granules, powders, ointments, drinks or injectable solutions.

The composition of the present invention may be prepared as a pharmaceutical formulation according to a conventional method. In preparation of the formulation, the active ingredient is preferably mixed or diluted with a carrier or enclosed within a carrier which is in the form of a container. When the carrier serves as a diluent, it may be a solid, semi-solid or liquid material which acts as a vehicle, excipient or medium for the active ingredient. Thus, the formulation can be in the form of tablets, pills, powders, sachets, elixirs, suspensions, emulsions, solutions, syrups, aerosols, soft and hard gelatin capsules, sterile injectable solutions, sterile packaged powders, etc.

Examples of suitable carriers, excipients and diluents include lactose, dextrose, sucrose, sorbitol, mannitol, calcium silicate, cellulose, methyl cellulose, microcrystalline cellulose, polyvinylpyrrolidone, water, methylhydroxybenzoate, propylhydroxybenzoate, talc, magnesium stearate and mineral oil. The formulations can additionally include fillers, anti-clumping agents, lubricating agents, wetting agents, flavoring agents, emulsifying agents, preserving agents, etc. The composition of the present invention may be formulated by a method well known in the art so as to provide quick, sustained or delayed release of the active ingredient after administration to mammals.

The pharmaceutical composition of the present invention may be administered by various routes, including oral, transdermal, subcutaneous, intravenous, intraperitoneal, intramuscular, topical, patch and iontophoresis routes. Among them, topical application and oral administration are preferred.

For humans, the usual daily dose of the active ingredient may be in the range of 1-100 mg/kg weight, preferably 5-70 mg/kg weight, and may be administered once or several times a day. It is to be understood, however, that the actual dose of the active ingredient is determined depending on various factors, including the disease to be treated, the route of administration, the patient's age, sex and weight, and the severity of the disease. Thus, the dose is not intended to limit the scope of the present invention in any way.

MODE FOR INVENTION

Hereinafter, the present invention will be described in detail with reference to examples, but the scope of the present invention is not limited to these examples.

Example 1

Preparation of Extract of Dried Ginseng Berries

1. Pretreatment of Ginseng Berries

Raw ginseng berries were harvested, and the seeds were separated and removed therefrom. Then, the flesh and skin of the ginseng berries were dried in sunlight or hot air, thereby preparing a dried ginseng berry material.

2. Preparation of Ginseng Berry Extract 1 kg of the dried ginseng berry material was added to 3 L of ethanol and extracted at room temperature or under reflux. Then, the extract was filtered, and then concentrated under reduced pressure at a temperature of 40 to 45° C., thereby obtaining 300 g of a ginseng berry extract.

Example 2

Preparation of Extract of Raw Ginseng Berries

1. Pretreatment of Ginseng Berries

Raw ginseng berries were harvested, and the seeds were separated and removed therefrom. Then, the flesh, juice and skin of the ginseng berries were collected and used as a ginseng berry material.

2. Preparation of Ginseng Berry Extract 1 kg of the ginseng berry material (i.e., a mixture of flesh, juice and skin) was added to 3 L of ethanol and extracted at room temperature or under reflux. Then, the extract was filtered, and then concentrated under reduced pressure, thereby obtaining 30 g of a ginseng berry extract.

Comparative Example 1

Preparation of Ginseng Root Extract

A ginseng root extract was prepared in the same manner as described in Example 1, except that ginseng roots were used instead of the ginseng berries.

Experimental Example 1

Comparison of Components of Ginseng Berry Extract

Analysis of Ginsenosides (Ginseng Saponins) of Ginseng Berries and Ginseng Roots Ginseng berry extracts and a ginseng root extract were prepared in Examples 1 and 2 and Comparative Example 1, respectively. These extracts were treated with ether to remove oil-soluble components, and then crude saponins were extracted with butanol (BuOH) and concentrated. The ginsenosides of the concentrated materials were analyzed through HPLC, and the results of the analysis are shown in FIG. 1 and Table 1 below.

TABLE 1

|  | Example 1 | Example 2 | Comparative Example 1 |
|---|---|---|---|
| Crude saponin content (dry weight) | 33.42% | 31.08 | 16.70% |
| PD/PT ratio | 0.73 | 0.69 | 3.23 |

Figure 1:
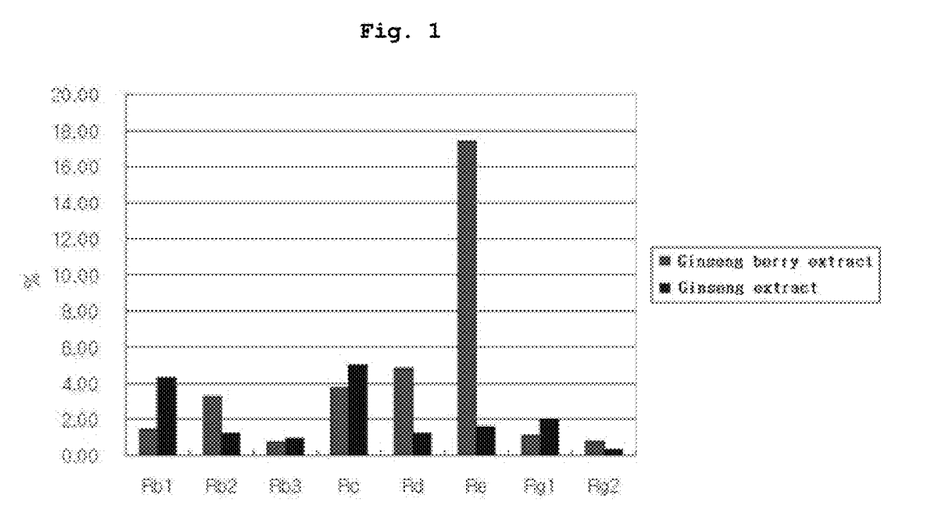
FIG. 1 is a graph showing analysis results for the ginsenosides of a ginseng berry extract of Example 1 and a ginseng extract.

As can be seen in FIG. 1 and Table 1 above, the ginseng berry extracts prepared in Examples 1 and 2 had a crude saponin content that was about 2-fold higher than that of the ginseng root extract prepared in Comparative Example 1.

When the ginsenosides were divided into the PD (protopanaxadiol) class "ginsenosides Rb1, Rb2, Rc and Rd", and the PT (protopanaxatriol) class "ginsenosides Re, Rg1 and Rg2", the PD/PT ratios of the extracts of Examples 1 and 2 were 0.73 and 0.69, respectively, which were smaller than 1, whereas the PD/PT ratio of the extract of Comparative Example 1 was 3.23, which was greater than 1, suggesting that the ginseng berry extracts and the ginseng root extract show distinct differences and characteristics with respect to the compositions of PD and PT of the ginsenosides.

Analysis of Mineral Components of Ginseng Berry Extract

In order to examine whether the ginseng berry extract prepared in Example 1 has the characteristics of berries, which differ from those of ginseng roots, the analysis of minerals including vitamins was carried out. The results of the analysis are shown in Table 2 below.

TABLE 2

| Components | Contents Example 1 | Contents Example 2 | Components | Contents Example 1 | Contents Example 2 |
|---|---|---|---|---|---|
| Potassium (mg/100 g) | 5865.57 | 4977.50 | Magnesium (mg/100 g) | 354.38 | 297.54 |
| Calcium (mg/100 g) | 819.26 | 914.22 | Zinc (mg/100 g) | 178.49 | 201.25 |
| Iron (mg/100 g) | 59.31 | 52.11 | Vit. A (μg/100 g, RE) | 213.11 | 145.85 |
| Phosphorus (mg/100 g) | 187.17 | 156.95 | Vit. $B_1$ (mg/100 g) | 12.29 | 10.09 |
| Vit. $B_2$ (mg/100 g) | 8.45 | 5.05 | Vit. $B_6$ (mg/100 g) | 10.50 | 15.44 |
| Vit. C (mg/100 g) | 4.91 | 7.13 | Vit. E (mg/100 g, α-TE) | 23.61 | 31.25 |
| Vit. K (μg/100 g) | 232.12 | 129.82 | Niacin (mg/100 g, NE) | 5.76 | 2.01 |
| Pantothenic acid (mg/100 g) | 5.87 | 6.15 | Folic acid (μg/100 g) | 349.97 | 423.35 |

As can be seen in Table 2 above, the ginseng berry extract that is used in the present invention contained ginseng saponins in amounts larger than those in the ginseng root extract, and the properties of the saponins thereof were contrary to each other. Also, it could be seen that the ginseng berry extract was rich in the contents of vitamins and 16 minerals compared to the root ginseng extract.

From the above results, it is expected that the ginseng berry extract will exhibit effects different from those of the ginseng root extract, because the components and their contents of the ginseng berry extract significantly differ from those of the ginseng root extract. However, it is expected that the extract of dried ginseng berries (Example 1) and the extract of undried raw ginseng berries (Example 2) will exhibit similar effects, because the components and their contents of the extracts are similar.

Based on these results, the changes in the quality of life of women by the use of the ginseng berry extract of Example 1 were observed and evaluated.

Experimental Example 2

Evaluation of Effects on Improvement in Quality of Life and Health of Women

The change in health before and after administration of the ginseng berry extract was evaluated in the following manner.

A 700 mg tablet (50%: 350 mg of the ginseng berry extract; and 50%: excipient, microcrystalline cellulose, etc.), which has a 50% content of the ginseng berry extract prepared in Example 1 and having a ginsenoside Re content of 10% or more, was prepared and used as a test sample. The prepared tablets were administered together with water to 18 women in their 20-30s and 25 women in their 40-50s (28 of the women were married) at a single dose of two tablets twice a day for 4 weeks, and questionnaire evaluation about the changes in usual health-related symptoms and inconvenience was carried out before and after administration of the tablets in the following manner.

The questionnaire evaluation was performed in the following manner. The evaluation was performed by allowing the subjects to answer to the questionnaire consisting of four domains before and after administration of the ginseng berry extract. In domain 1, the number of items regarding uncomfortable symptoms related to general physical health was reported for comparison between before and after administration of the ginseng berry extract. In domain 2, the subjects were allowed to report the severity of each of 21 chronic fatigue symptoms on a four-point scale (from score 0 to score 3). In domain 3, the subjects were allowed to report about the psychological general well-being index (PGWBI; evaluation of the physical health, psychological health, stress and the like of the subjects). In domain 4, the subjects were allowed to report about the female sexual function index (FSFI; evaluation of sexual satisfaction). Through this questionnaire evaluation, the effects of the ginseng berry extract on the health of women were evaluated.

1. Evaluation of Degree of Improvement in General Physical Health (Domain 1)

In domain 1, the subjects were allowed to report about symptoms felt for 4 weeks during which the ginseng berry extract was administered (multiple checks available).

Evaluation Items
peripheral circulatory disturbance
dry skin
fatigue
dry mouth
chest discomfort or tightness
bowel health
sleep disorder
indigestion
facial flushing
menstrual irregularity.

Figure 2:
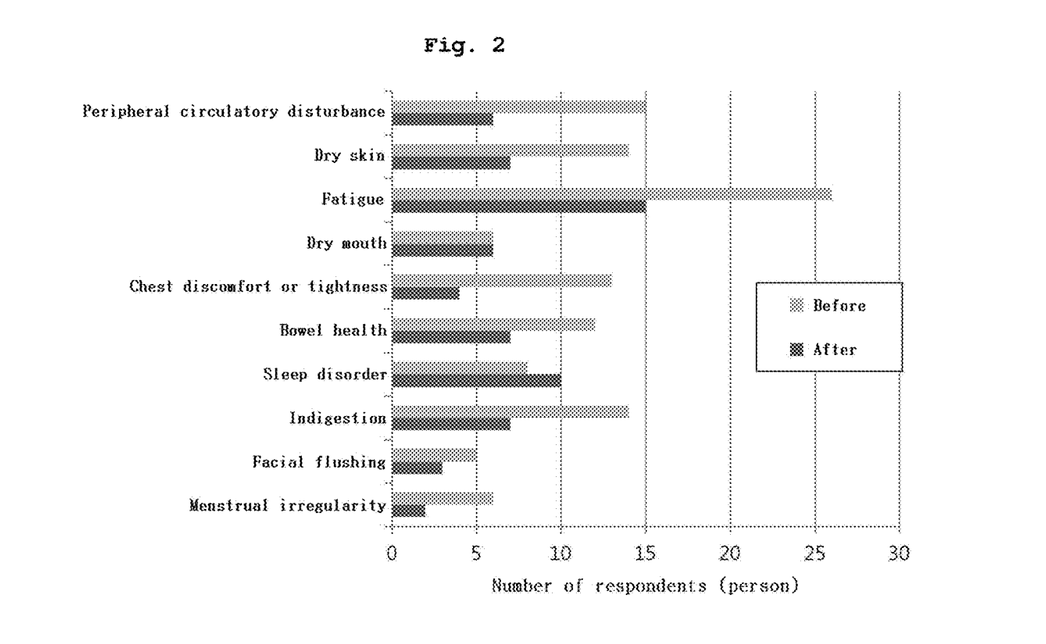
FIG. 2 shows the results of evaluating the degree of improvement in general physical health by administration of a ginseng berry extract.

The results of evaluation of the above items are shown in FIG. 2.

Referring to FIG. 2, it can be seen that typical symptoms, including peripheral circulatory disturbance (tingling sensation in hands and feet), dry skin, chest discomfort, constipation and indigestion, were reduced.

2. Self-Diagnosis of Chronic Fatigue (Domain 2)

Among the evaluation items in the above section 1, changes in the symptom expressed as "fatigue" need to be analyzed in detail. Thus, when the questionnaire of the above section 1 was performed, the subjects were allowed to answer to 21 items shown in Table 3 below with respect to the change between before and after administration of the ginseng berry extract, and were allowed to select the items thought to best represent their own status for 4 weeks of administration of the ginseng berry extract. Herein, each item was scored as 0 when there was no symptom, and scored as 3 when the symptom was frequently felt, such that the sum of the scores showed a distribution of 0-63.

TABLE 3

Self-Report Questionnaires about Chronic Fatigue

| No. | Question | None | About once two weeks | About once a week | Frequent |
|---|---|---|---|---|---|
| 1 | Fatigue does not disappear even after sufficient rest. | | | | |
| 2 | The body has a slight fever or feels a chill. | | | | |
| 3 | The body feels heavy while the muscle of the whole body has pain. | | | | |
| 4 | Deep sleep does not occur. | | | | |
| 5 | The speed of thinking is slower than former | | | | |
| 6 | Frequent depressed feeling | | | | |
| 7 | Severe headache | | | | |
| 8 | Have a swollen and sore throat while feeling foreign sensation in the throat. | | | | |
| 9 | Often nervous | | | | |
| 10 | The energy of the body is used up | | | | |
| 11 | The back of the neck feels tight. | | | | |
| 12 | The sight grows dim. | | | | |
| 13 | Frequent urination | | | | |
| 14 | Feel nausea and giddy. | | | | |
| 15 | Rapid heartbeat | | | | |
| 16 | The eyes are dry. | | | | |
| 17 | The mouth is dry. | | | | |
| 18 | Feces are irregular (watery or hard). | | | | |
| 19 | Knuckles are swollen. | | | | |
| 20 | sweating during sleep. | | | | |
| 21 | facial hot flashes | | | | |

The results of the evaluation are shown in Table 4 below and FIG. 3.

TABLE 4

Change in Self-Diagnosis Score of Chronic Fatigue Before and After Administration of Ginseng Berry Extract, Paired T-Test (N = 43, P-Value = 0.001)

| | Mean | SD | |
|---|---|---|---|
| Before administration | 18.19 | 13.03 | Decrease in mean chronic fatigue index of 6.10 |
| After administration | 12.09 | 10.70 | |

Figure 3A:
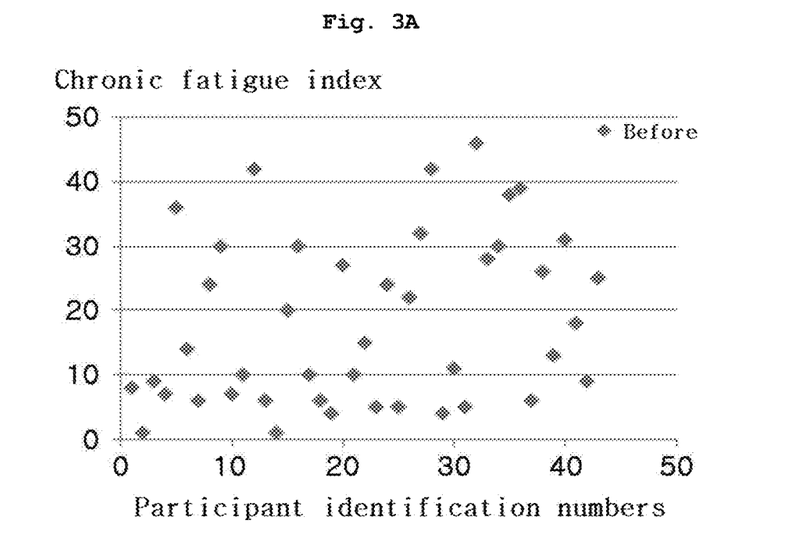
FIGS. 3A and 3B show the results of evaluating the degree of alleviation of chronic fatigue by administration of a ginseng berry extract.
Figure 3B:
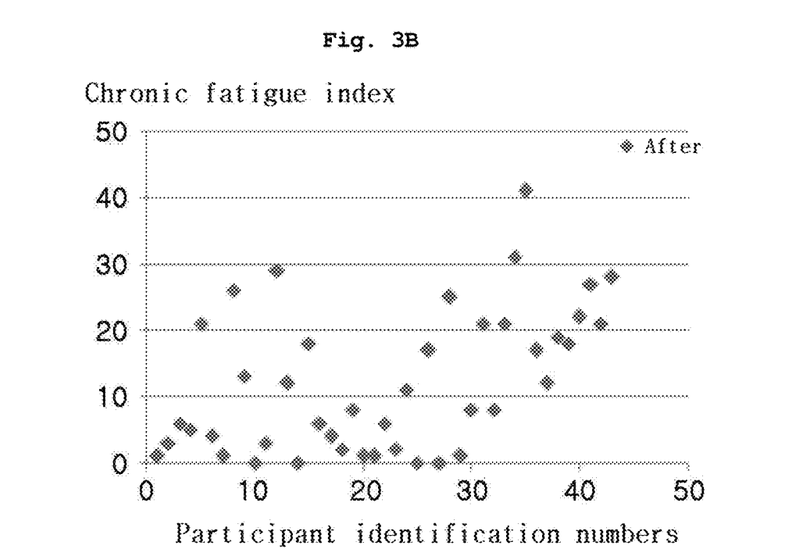

As can be seen in Table 4 above and FIG. 3, the self-diagnosis score of chronic fatigue for the subjects decreased from 18.19 before administration to 12.09 after administration (34% decrease).

3. Evaluation of PGWBI Index (Domain 3)

The PGWBI (psychological general well-being index; general psychological health index) was developed by Harold Dupuy (1984, USA) in order to express and measure the degrees of well-being and distress felt by individuals, and consists of 22 health-related QOL (quality of life) items. It was introduced in Europe in 1990s, and has been applied in various languages and countries. The PGWBI evaluates HRQoL across six domains: anxiety, vitality, depressed mood, self-control, positive well-being, and general health.

To evaluate the PGWBI index, the changes in the above-mentioned six domains before and after administration of the ginseng berry extract were measured, and each domain was scored on a scale of 0 to 5, and the sum of the scores of the domains was used as a PGWBI score (from 0 to 30). A score of 0 for each item indicates a low or bad QOL, and a score of 5 for each item indicates the highest or best QOL state. The overall quality of life was measured by averaging the scores of each domain and calculating the sum of the scores.

Specific evaluation items are as follows. Among them, questions associated with anxiety are Nos. 5, 8, 17, 19 and 22; questions associated with depressed mode are Nos. 3, 7 and 11; questions associated with positive well-being are Nos. 1, 9, 15 and 20; questions associated with self-control are Nos. 4, 14 and 18; questions associated with general health are Nos. 2, 10 and 13; and questions associated with vitality are Nos. 6, 12, 16 and 21.

1. How was your feeling during the last week?
 0) Best
 1) very good
 2) Good most of the time
 3) A lot of change in the mood; I felt alternately elated and overwrought.
 4) Bad most of the time
 5) Very bad 2. Did you feel uncomfortable week due to any kinds of diseases, or pain or worries for your health during the last week?
 0) Felt uncomfortable everyday.
 1) Felt uncomfortable almost everyday.
 2) Felt uncomfortable for half of the time.
 3) Felt uncomfortable sometimes, but not for half of the time.
 4) Hardly felt uncomfortable.
 5) Never felt uncomfortable.

3. Have you felt depressed for the last week?
 0) Yes, I've felt depressed to die.
 1) Yes, I've felt so depressed that I could not be interested in anything.
 2) Yes, I felt almost every day.
 3) Yes, I felt quite depressed several times.
 4) Yes, I felt a little depressed sometimes.
 5) No, I have not felt depressed at all.

4. Do you think that you controlled your behavior, thought and feeling very well during the last week?
 5) Yes, I controlled them completely.
 4) Yes, I controlled them well most of the time.
 3) I can say that I controlled them generally.
 2) No, I did not control them so well.
 1) No, I got angry and failed to control my feeling sometimes.
 0) No, I could not control my feeling.

5. Did you get distressed because you got sensitive during the last week?
 0) I was so distressed that I could not do my work or enjoy my everyday life.
 1) I was distressed a lot.
 2) I was distressed considerably.
 3) I was distressed sometimes.
 4) I was not distressed so much.
 5) I was not distressed at all.

6. How active and energetic was your life during the last week?
 5) It was quite an active and energetic life.
 4) It was considerably active most of the time.
 3) There was a considerable change; sometimes it was active and then it was not so active.
 2) Generally, I could not live an active life.
 1) It was not active most of the time.
 0) It was not an active life at all. I was exhausted.

7. Did you feel sad or disappointed during the last week?
 5) Not at all
 4) Very rarely.
 3) Sometimes.
 2) Fairly.
 1) Quite often.
 0) Always 8. How often and how much did you feel nervous during the last week?
 0) I always felt nervous severely.
 1) I felt nervous most of the time.
 2) I did not feel nervous generally, but felt nervous several times.
 3) I felt nervous a little sometimes.
 4) I did not feel nervous most of the time.
 5) I did not feel nervous at all.

9. How much did you feel happy, joyful and satisfied during the last week?
 5) I felt quite happy.
 4) I felt happy most of the time.
 3) I felt happy on the whole.
 2) I felt happy sometimes and I felt unhappy sometimes.
 1) I was unhappy on the whole.
 0) I was very unhappy.

10. Was your health condition good enough for you to do the things that you should do or want to do well during the last week?
 5) Yes, it was quite good.
 4) It was good most of the time.
 3) There were times when I could not do what I should do and what I want to do due to health problems.
 2) I could take care of myself.
 1) I needed other people's help to take care of myself.
 0) I required other people's help to do almost all things that I should do.

11. Have you felt sad, gotten exhausted or despaired to have doubt about life during the last week?
 0) I severely despaired to give up on life.
 1) I quite despaired.
 2) I considerably despaired.
 3) I painfully despaired sometimes.
 4) I despaired a little.
 5) I did not despair at all.

12. Did you get refreshed after waking up during the last week?
 0) Not at all.
 1) Very rarely.
 2) Sometimes.
 3) Often
 4) Most of the time.
 5) Always 13. Did you worry about your health during the last week?
 0) I worried about it very much.
 1) I worried about it considerably.
 2) I worried about it a little.
 3) I worried about it sometimes, but it was not serious.
 4) I did not worry about it so much.
 5) I did not worry about it at all.

14. Did you worry that you would lose control of your behavior during the last week?
 5) Not at all.
 4) No so much.
 3) I worried sometimes, but it was not serious.
 2) I worried a little sometimes.
 1) I am quite worried sometimes.
 0) I often worried it very much.

15. Was the last week filled with interesting things for you?
 0) Not at all.
 1) It was so only very rarely.
 2) It was so sometimes.
 3) It was often so.
 4) It was so most of the time.
 5) I was always so.

16. How actively and how diligently did you live your life during the last week?
 5) I lived a very diligent and active life always.
 4) I lived an active life most of the time.
 3) I lived a diligent and active life relatively.
 2) I lived a relatively boring and lazy life.
 1) I lived a boring and lazy life most of the time.
 0) I lived a boring and lazy life always.

17. Did you feel nervous, worried or confused during the last week?
 0) It was so to such a degree that I felt sick.
 1) It was quite so.
 2) It was considerably so.
 3) It was so to such an extent that I got distracted sometimes.
 4) It was hardly so.
 5) Not at all.

18. Did you feel secure and proud during the last week?
 0) Not at all.
 1) Very rarely.
 2) Sometimes.
 3) Often
 4) I felt so most of the time.
 5) I felt so always.

19. Did you feel comfortable during the last week?
 5) I felt comfortable always.
 4) I felt comfortable most of the time.
 3) I felt comfortable generally, but I felt considerably nervous sometimes.
 2) Generally, I felt quite nervous, but sometimes, I felt quite comfortable.
 1) I felt severely tensed most of the time.
 0) I felt severely tensed all week.

20. Did live a cheerful life during the last week?
 0) I did not live a cheerful life at all.
 1) My life was cheerful very rarely.
 2) My life was cheerful sometimes.
 3) My life was often cheerful.
 4) My life was cheerful most of the time.
 5) My life was cheerful always.

21. Did you feel tired or very exhausted during the last week?
 5) Not at all.
 4) I did so very rarely.
 3) I did so sometimes.
 2) I did so often.
 1) I did so most of the time.
 0) I did so always.

22. Did you feel stressed or pressured during the last week?
 0) Yes, I felt stressed unbearably.
 1) Yes, I felt considerably stressed.
 2) Yes, I felt more stressed than usual.
 3) Yes, I felt stressed as usual.
 4) Yes, I felt stressed a little.
 5) Not at all.

The results of the evaluation are shown in Table 5 below.

TABLE 5

Change in PGWBI Index Before and After Administration of Ginseng Berry Extract, Paired T-Test (N = 43)

| Items | Range | Mean ± S.D. before administration | Mean ± S.D. after administration | Difference | P-value |
|---|---|---|---|---|---|
| Anxiety | 0-5 | 3.86 ± 1.28 | 4.35 ± 0.84 | 0.49 | 0.013 |
| Vitality | 0-5 | 2.63 ± 0.98 | 3.21 ± 0.86 | 0.58 | 0.001 |
| Depressed mood | 0-5 | 3.14 ± 0.94 | 3.79 ± 0.89 | 0.65 | 0.001 |

TABLE 5-continued

Change in PGWBI Index Before and After Administration
of Ginseng Berry Extract, Paired T-Test (N = 43)

| Items | Range | Mean ± S.D. before administration | Mean ± S.D. after administration | Difference | P-value |
|---|---|---|---|---|---|
| Self-control | 0-5 | 2.02 ± 1.28 | 2.37 ± 1.25 | 0.35 | 0.092 |
| Positive well-being | 0-5 | 2.09 ± 1.29 | 2.84 ± 1.34 | 0.74 | 0.001 |
| General health | 0-5 | 2.84 ± 1.15 | 3.72 ± 0.77 | 0.88 | 0.000 |
| PGWBI score | 0-30 | 16.58 ± 4.59 | 20.28 ± 4.15 | 3.70 | 0.000 |

As can be seen in Table 5 above, the PGWBI increased from 16.58 before administration of the ginseng berry extract to 20.28 after administration of ginseng berry extract (22% increase). Particularly, the best effect on improvement in the PGWBI was observed in the positive well-being domain and the general health domain. Thus, it can be concluded that the ginseng berry extract improves the quality of life by increasing the PGWBI index.

4. Evaluation of FSFI Index (Domain 4)

The FSFI (female sexual function index) was developed by Dr. Raymond Rosen for the purpose of clinical research in order to measure the sexual function and satisfaction of women (Bayer AG, Zonagen Inc. funding). It is a measure that measures six domains: sexual desire, arousal, lubrication, orgasm, satisfaction, and pain.

In this Experimental Example, in order to evaluate the FSFI index in a simple manner, the changes in four of the above-mentioned six domains before and after administration of the ginseng berry extract were evaluated. Each domain was scored on a scale of 0-5 or 1-5 as shown in Table 6 below, and a weight factor was given to each domain such that the sum of the scores was 1-8.5. The sum of the scores of the domains was used as a FSFI score.

Specific evaluation items are as follows. Among them, a question associated with sexual desire is No. 1; a question associated with arousal is No. 2; a question associated with orgasm is No. 3; and a question associated with satisfaction is No. 4.

1. How often did you feel interested or feel sexual desire during the last 4 weeks?
   1) Always
   2) Most of the time
   3) Moderately
   4) Sometimes
   5) Hardly 2. How was your sexual excitement during sex (including intercourse) during the last 4 weeks?
   0) There was no sex.
   1) Quite high.
   2) High
   3) Moderate
   4) Low
   5) Quite low 3. How often have you felt orgasm at the time of sexual stimuli or intercourse during the last 4 weeks?
   0) There was no sex.
   1) Always
   2) Most of the time.
   3) Moderately.
   4) Sometimes
   5) Hardly 4. How often were you satisfied with your sex life during the last 4 weeks?
   1) Always
   2) Most of the time
   3) Moderately
   4) Mostly, I was not satisfied.
   5) I was hardly satisfied.

The results of the evaluation are shown in Table 6 below.

TABLE 6

Change in FSFI Index Before and After Administration
of Ginseng Berry Extract, Paired T-Test (N = 28)

| Domain | range | Weight factor | Mean ± S.D. before administration | Mean ± S.D. after administration | Difference | P-value |
|---|---|---|---|---|---|---|
| Sexual desire | 1-5 | 0.6 | 2.32 ± 1.19 | 2.46 ± 0.88 | 0.14 | 0.381 |
| Arousal | 0-5 | 0.3 | 2.25 ± 1.55 | 2.79 ± 1.37 | 0.54 | 0.033 |
| Orgasm | 0-5 | 0.4 | 2.46 ± 1.95 | 3.04 ± 1.64 | 0.57 | 0.033 |
| Satisfaction | 1-5 | 0.4 | 2.89 ± 1.62 | 3.39 ± 1.45 | 0.50 | 0.06 |
| FSFI score | 1-8.5 | | 4.21 ± 2.34 | 4.89 ± 1.90 | 0.68 | 0.031 |

As can be seen in Table 6 above, the FSFI index increased from 4.21 before administration of the ginseng berry extract to 4.89 after administration of the ginseng berry extract (16.2% increase). Particularly, it can be seen that the ginseng berry extract can improve the domains of arousal, orgasm and satisfaction in the sex life of married women. Thus, it can be concluded that the ginseng berry extract can assist in improvement in the quality of life by increasing the FSFI index.

Experimental Example 3

Correlation Between PGWBI and FSFI

Based on the results of Experimental Examples 2-3 and 2-4, the correlation between the PGWBI and the FSFI was analyzed.

Figure 4A:
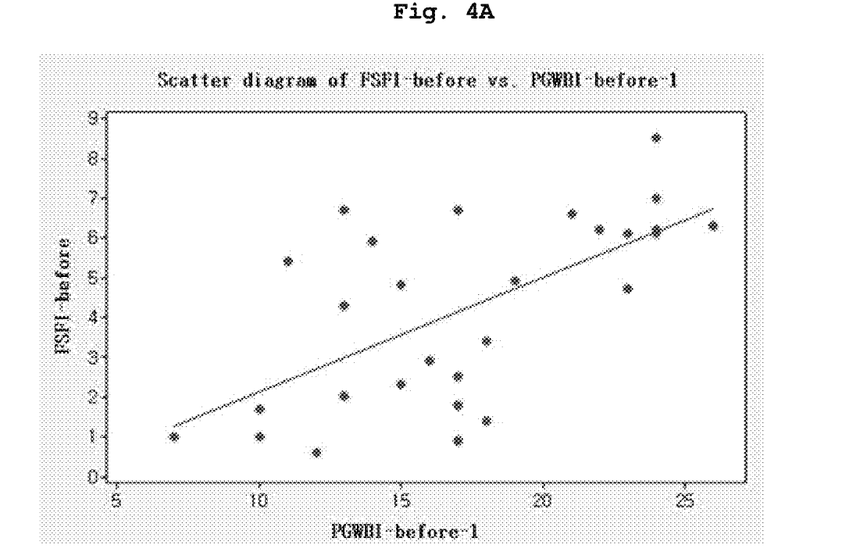
FIGS. 4A and 4B are graphs showing the correlation between PGWBI index and FSFI index.
Figure 4B:
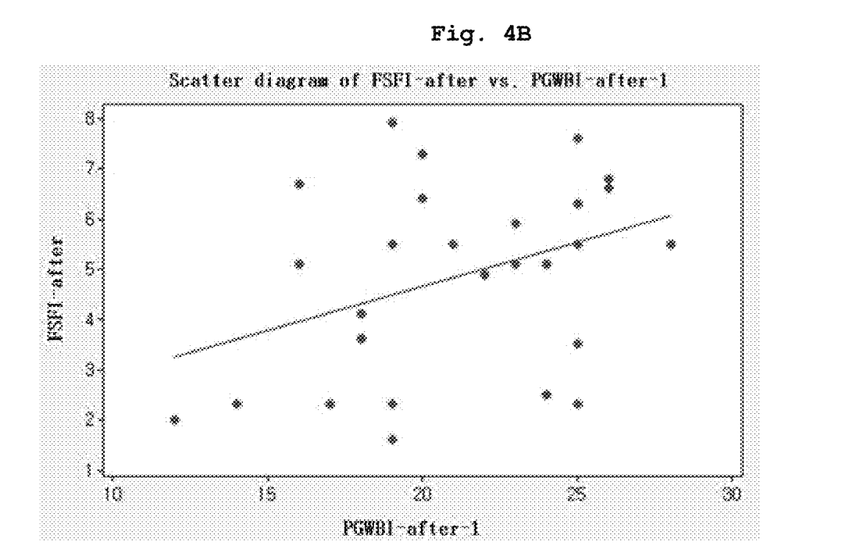

The results of the PGWBI that expresses the psychological stress status while recognizing their own health status were proportional to the results of the FSFI that measures the sexual function and satisfaction of women, as shown in FIG. 4.

The happiness index of women can be expressed by the degree of improvement in the quality of life, such as PGWBI and FSFI. As can be seen in FIG. 4, the two major factors (PGWBI and FSFI) showed a high correlation therebetween before and after their improvement by the ginseng berry extract, and thus can be considered essential evaluation factors.

Experimental Example 4

Evaluation of Improvement in General Health Status

In addition to the results of Experiment Example 2, the subjects reported that, after administration of the ginseng berry extract, fatigue was alleviated, psychological stability could be obtained, the skin conditions were improved, tingling sensation in hands and feet disappeared, and menopausal symptoms were alleviated.

The invention claimed is:

1. A method for alleviating menopausal symptoms in a woman in need thereof, comprising administering an effective amount of a composition comprising, as a sole active ingredient, a ginseng berry extract to the woman, wherein the ginseng berry extract is an ethanol extract of a ginseng berry from which seeds are removed, wherein menopausal symptoms include at least one of peripheral circulatory disturbance, dry skin, chronic fatigue, dry mouth, chest discomfort, bowel health, sleep disorder, indigestion, facial flash, menstrual irregularity, depressed mood, and decreased sexual function.

2. The method of claim 1, wherein the alleviating menopausal symptoms is a promotion of peripheral circulation.

3. The method of claim 1, wherein the alleviating menopausal symptoms is an alleviation of chronic fatigue.

4. The method of claim 1, wherein the alleviating menopausal symptoms is an improvement in depressed mood.

5. The method of claim 1, wherein the alleviating menopausal symptoms is an improvement of sexual function of the woman.

6. The method of claim 5, wherein the improvement of sexual function comprises an increases in sexual desire, arousal, orgasm, and/or satisfaction.

* * * * *